United States Patent [19]

Cooper et al.

[11] Patent Number: 4,954,487
[45] Date of Patent: Sep. 4, 1990

[54] PENETRATING TOPICAL PHARMACEUTICAL COMPOSITIONS

[75] Inventors: Eugene R. Cooper; Maurice E. Loomans, both of Cincinnati; Richard R. Wickett, Ross, all of Ohio

[73] Assignee: The Procter & Gamble Company, Cincinnati, Ohio

[21] Appl. No.: 312,354

[22] Filed: Feb. 15, 1989

Related U.S. Application Data

[60] Continuation of Ser. No. 56,344, May 27, 1987, abandoned, which is a division of Ser. No. 516,005, Jul. 20, 1983, abandoned, which is a continuation of Ser. No. 296,706, Aug. 27, 1981, abandoned, which is a continuation-in-part of Ser. No. 167,167, Jul. 9, 1980, abandoned, which is a continuation-in-part of Ser. No. 149,104, May 12, 1980, abandoned, and a continuation-in-part of Ser. No. 1,974, Jan. 8, 1979, abandoned.

[51] Int. Cl.$^5$ .............................................. A61K 31/60
[52] U.S. Cl. ...................................... 514/159; 514/420; 514/569; 514/570; 514/947
[58] Field of Search ............... 514/159, 420, 569, 570, 514/947

[56] References Cited

U.S. PATENT DOCUMENTS

| | | | |
|---|---|---|---|
| 2,990,331 | 6/1961 | Neumann et al. | 167/65 |
| 3,535,422 | 10/1970 | Cox et al. | 424/164 |
| 3,592,930 | 7/1971 | Katz et al. | 424/243 |
| 3,888,995 | 6/1975 | Katz et al. | 424/358 |
| 3,924,004 | 12/1975 | Chang et al. | 424/358 |
| 4,006,218 | 2/1977 | Sipos | 424/54 |
| 4,070,462 | 1/1978 | Ecker | 424/243 |
| 4,075,353 | 2/1978 | Mandy et al. | 424/338 |
| 4,126,681 | 11/1978 | Reller | 424/234 |
| 4,299,826 | 11/1981 | Luedders | 514/947 X |
| 4,309,414 | 1/1982 | Inagi et al. | 424/81 |
| 4,537,776 | 8/1985 | Cooper | 514/424 |
| 4,552,872 | 11/1985 | Cooper et al. | 514/175 |
| 4,557,934 | 12/1985 | Cooper | 424/128 |

FOREIGN PATENT DOCUMENTS

1072009 2/1980 Canada .
2514873 10/1976 Fed. Rep. of Germany .
1133800 11/1968 United Kingdom .
1594314 7/1981 United Kingdom .

OTHER PUBLICATIONS

Lachman et al.–The Theory & Practice of Industrial Pharmacy, 2nd ed., 1926, pp. 217–220.
Chemical Abstracts, vol. 92, cite 153,181j, p. 412 (1980), Nagai, et al.
H. Barnes, et al., *Br. J. Derm.*, 92, 459 (1975).
P. J. W. Ayres, et al., *Br. J. Derm.*, 99, 307 (1978).
Schaaf & Gross, *Dermatologica*, 106, 357 (1953).
J. Zatz, et al., *J. Pharm. Sci.*, 67, 789 (1978).
S. K. Chandrasekaran, et al., *J. Pharm. Sci.*, 67, 1370 (1978).
B. Idson, *Cosmetics & Toiletries*, 95, 59 (1980).
M. M. Reiger, *Cosmetics & Toiletries*, 94, 32–37 (1979) and 95, 26–38 (1980).
J. A. Sands, et al., "Antiviral Effects of Fatty Acids & Derivatives: Lipid–Containing Bacteriophages as a Model System", Chapter 8 of *Symposium on the Pharmacological Effects of Lipids*, Jon J. Kabara (ed.) 1978, pp. 75–95.
Chemical Abstracts, vol. 79, cite 122,308h, p. 65 (1973), Dugard & Scheuplein.
Chemical Abstracts, vol. 79, cite 122,309j, p. 65 (1973), Scheuplein & Blank.

*Primary Examiner*—Leonard Schenkman
*Attorney, Agent, or Firm*—Milton B. Graff, IV; George W. Allen; Steven J. Goldstein

[57] ABSTRACT

A large group of lipophilic, pharmacologically active compounds can be effectively delivered across intact skin by applying them topically in a binary, penetration-enhancing vehicle containing (1) a $C_3$–$C_4$ diol, diol ester, or diol ether and (2) a cell envelope-disordering compound. This vehicle provides surprising enhancement of skin penetration for the pharmacological active, compared to either component alone.

8 Claims, No Drawings

PENETRATING TOPICAL PHARMACEUTICAL COMPOSITIONS

This is a continuation of U.S. Ser. No. 056, 344, filed on May 27, 1987, which is in turn a division of U.S. Ser. No. 516,005, filed July 20, 1983, which is in turn a continuation of U.S. Ser. No. 296,706, filed Aug. 27, 1981, which is turn a continuation-in-part of U.S. Ser. No. 167,167, filed July 9, 1980, which is in turn a continuation-in-part of U.S. Ser. No. 149,104, filed May, 12, 1980, which is in turn a continuation-in-part of U.S. Ser. No. 001,974, filed Jan. 8, 1979 all now abandoned.

TECHNICAL FIELD

This invention relates to pharmaceutical compositions containing a penetrating vehicle which markedly enhances the delivery of the drug active across human skin.

Because of the accessibility and large area of the skin, it has long been considered a promising route for the administration of drugs, whether dermal, regional, or systemic effects are desired.

The advantages of the topical route of drug administration include: avoidance of the risks and inconvenience of parenteral treatment; avoidance of the variable absorption and metabolism associated with oral treatment; continuity of drug administration, permitting use of pharmacologically active agents with short biological half-lives; potential reduction of gastrointestinal irritation in systemic administration; and treatment of cutaneous manifestations of diseases usually treated systemically.

However, the impermeability of skin is well-known, serving as a barrier to ingress of pathogens and toxic chemicals, and egress of physiologic fluids. This impermeability is the result of normal physiologic changes in developing skin. A typical cell in the epidermis is formed in the basal layer. It typically takes approximately thirty days for a cell to migrate from the basal layer of the epidermis to sloughing off and discarding at the outer layers of the stratum corneum. As the cell migrates outward from the basal layer, it progressively keratinizes until it is relatively impermeable. The result is the stratum corneum, an extremely thin surface layer (10 microns) with substantial barrier properties. The cell envelopes of the cells in the stratum corneum tend to be mainly polar lipids, such as ceramides, sterols, and fatty acids while the cytoplasm of stratum corneum cells remains polar and aqueous. Despite the close packing of the cells, some 15% of the stratum corneum is intercellular and, generally, lipid based. It is generally recognized that over the very short term, penetration occurs through the hair follicles and the sebaceous apparatus; long-term penetration occurs across cells (non-polar route). Poor penetration of many drugs across the epidermal lipid barrier has, until now, frustrated attempts to deliver clinically significant doses of many drugs by the topical route.

The present invention relates to the discovery that, by increasing the disorder of the lipid portion of the cell envelopes in the stratum corneum, the lipid packing of the envelope can be disrupted, thereby liquifying it and allowing lipid soluble drugs to pass through the stratum corneum. In particular, it has been discovered by differential scanning calorimetry that certain binary skin penetration enhancement systems eliminate the TM-2 peak associated with melting of cell envelope lipids.

The enhanced penetration provided by the present invention now makes the topical mode of treatment practical by percutaneously delivering clinically effective doses of active drug.

BACKGROUND ART 1,2-propanediol ("propylene glycol") and the $C_{10}$–$C_{14}$ alcohols have been used, separately, in cosmetic and pharmaceutical formulations. In particular, propylene glycol has been described in several articles in the literature as enhancing the penetration of certain pharmacologically active agents, such as the corticosteroids.

U.S. Pat. No. 3,535,422, Cox, et al., Oct. 20, 1970 relates to stable benzoyl peroxide compositions containing organic emollients. The compositions include emollients selected from the $C_4$–$C_{20}$ aliphatic alcohols, $C_2$–$C_3$ glycols, $C_{12}$–$C_{20}$ fatty acids and their esters, and mixtures thereof.

U.S. Pat. No. 4,070,462, Ecker, issued Jan. 24, 1978, describes topical steroid compositions containing 6% propylene glycol and 1% propylene glycol monosterate.

Canadian No. 1,072,009, describes topical antimicrobial compositions containing $C_5$–$C_{10}$ straight chain alcohols or $C_{17}$ branched chain alcohols in which the longest chain is $C_5$–$C_{10}$.

CA 92:153,181j; describes an indomethacin ointment containing 10% propylene glycol and 1.1% diisopropanolamine.

U.S. Pat. No. 2,990,331, Neumann, et al., issued June 27, 1961, describes tetracycline compositions containing carboxylic acid alkylolamides.

H. Barnes, et al., *Br. J. Derm.* 93, 459 (1975) describe testing of fluocinonide and fluocinolone acetonide in a vehicle describes as fatty alcohol propylene glycol (FAPG).

P. J. W. Ayres, et al., *Br. J. Derm.*, 99, 307 (1978), report comparative skin penetration of cortisol from commercially available cortisol ointments.

Schaaf and Gross, *Dermatologica*, 106, 357 (1953) note that unsaturated fatty acids and $C_6$–$C_{14}$ saturated fatty acids are particularly active in provoking epidermal thickening.

J. Zatz, et al., *J. Pharm. Sci.*, 67, 789 (1978) study the effect of formulation factors on penetration of hydrocortisone through mouse skin.

S. K. Chandrasekaran, et al., *J. Pharm. Sci.*, 67, 1370 (1978) discuss the pharmacokinetics of drug permeation through human skin.

B. Idson, *Cosmetics & Toiletries*, 95, 59 (1980), states the factors affecting drug penetration and, consequently, in most cases effectiveness, are complex. He observes that the vehicle that provides ideal conditions for one drug may prove unsatisfactory for another. The author concludes that prediction is not simple and product suitability must be assessed by human trials. The same article indicates that Synalar Cream, a topical corticosteroid preparation, contains sorbitan monooleate and propylene glycol.

M. M. Rieger, *Cosmetics & Toiletries*, 94, 32–37 (1979) and 95, 26–38 (1980), provides reviews of current literature in the area of skin penetration.

J. A. Sands, et al., *The Pharmacological Effect of Lipids*, 76 (1978) report that fatty acids and fatty acid derivatives are agents which can "interact with lipids and membrane proteins" to inhibit reproduction of lipid containing bacteriophage in controlled studies. No mechanism or structure-function relationship is elucidated.

U.S. patent application Ser. No. 084,252, filed Oct. 12, 1979, describes a composition for the treatment of acne by using diisopropyl sebacate as a penetration enhancer for an erythromycin derivative in combination with an alcohol.

U.S. Pat. No. 2,990,331, Neumann, et al., describes the parenteral administration of tetracycline salts from a stable aqueous solution.

CA 79: 122,308, describes an electromagnetic study of n-alkyl ionic surfactants as aiding in human epidermis penetration.

DISCLOSURE OF THE INVENTION

The binary systems of this invention require, basically, a polar diol solvent, and a compound which disrupts the organized packing of cell envelope lipids. The latter ("envelope-disordering") compounds typically have bent chains, caused by cis-double bonds, branched chains, short chains, and the like. These compounds can be described by the formula $R^3$-X, where $R^3$ is a straight-chain alkyl of about 7 to about 16 carbon atoms, a nonterminal alkenyl (terminal alkenyls do not have a "kinked" structure) of about 7 to about 22 carbon atoms, or a branched chain alkyl of about 13 to about 22 carbon atoms, where X is —OH, —COOCH$_3$, —COOC$_2$H$_5$, —OCOCH$_3$, —SOCH$_3$, —COOCH$_2$CHOHCH$_3$, —COOCH$_2$CHOHCH$_2$OH, —P(CH$_3$)$_2$O, —COOC$_2$H$_4$OC$_2$H$_4$OH, —(OCH$_2$CH$_2$)$_m$OH, —COOCH(CHOH)$_4$CH$_2$OH, —COOCH(CHOH)$_4$CH$_2$OH, —COOR$^4$, or

where $R^4$ is —H, —CH$_3$, —C$_2$H$_5$, —C$_3$H$_7$ or —C$_2$H$_4$OH, $R^8$ is —H, —CH$_3$, —C$_2$H$_5$, —C$_3$H$_7$ or —C$_2$H$_4$OH, $R^9$ is —H, —CH$_3$, —C$_2$H$_5$, —C$_3$H$_7$ or —C$_2$H$_4$OH, and m is 2-6.

With the alkenols and alkenoic acids, at least one double bond must be in the cis-configuration, as mentioned; this requirement does not apply for the methyl sulfoxides, phosphine oxides, propylene glycol esters or glycerol esters, possibly because these head groups, while fairly short, are comparatively bulky, requiring greater spacing of the molecules, and thus causing additional disruption of the orderly lipid structure of the cell envelope.

Compounds of the foregoing category, which disrupt or disorder the lipid structure of stratum corneum cell envelopes, include, without limitation, the n-octyl, decyl, dodecyl, and tetradecyl alcohols; the methyl and ethyl esters of n-octanoic, decanoic, dodecanoic, tetradecanoic and hexadecanoic acid; the acetates of n-octanol, decanol, dodecanol, tetradecanol and hexadecanol, such as lauryl acetate and myristyl acetate; the methyl, ethyl, N,N-dimethyl, diethyl and-methyl ethyl amides of n-octanoic, decanoic, dodecanoic, tetradecanoic and hexadecanoic acids; the decenyl, dodecenyl, tetradecenyl, hexadecenyl, octadecenyl, eicosaenyl, and docosaenyl alcohols in which the double bond has the cis-configuration; cis-myristoleic, palmitoleic, oleic, linoleic, linolenic, arachidonic, and erucic acids; tetradecenyl methyl sulfoxide, hexadecenyl methyl sulfoxide, octadecenyl methyl sulfoxide, eicosenyl methyl sulfoxide, and docesenyl methyl sulfoxide; methyl cis-myristoleate, -palmitoleate, -oleate, -linoleate, -linolenate, -arachidonate, and -erucate; oleic isopropyl amide, dimethyl glycol oleate, polyethylene glycol 200 monolinoleate, dioxyethylene isostearyl ether, dioxyethylene oleyl ether, sorbitan monoleate, sorbitan monoisostearate, and ethyl isostearate; myristoleyl, palmitoleyl, oleyl, linoleyl, linolenyl, arachidonyl, and erucyl dimethyl phosphine oxides; isohexadecyl dimethyl phosphine oxide, isooctadecyl dimethyl phosphine oxide, isoeicosenyl dimethyl phosphine oxide, and isodocosyl dimethyl phosphine oxide; isohexadecyl monoethanolamide, isooctadecyl monoethanolamide, isoeicosyl monoethanolamide, and isodocosyl monoethanolamide: propylene glycol monoisopalmitate, propylene glycol monoisostearate, propylene glycol monoisoarchidate, propylene glycol monoisobehenate, glycerol monoisopalmitate, glycerol monoisostearate, glycerol monooesoarach, and glycerol monoisobehenate; and phytol, bactoprenol, geraniol, isophytol, and farnesol.

The diols, diol esters, and diol ethers ("diol compounds") useful herein can be represented by the formula

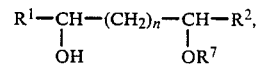

where $R^1$ is —H, —CH$_3$ or CH$_3$COO—, $R^2$ is —H or —CH$_3$, $R^7$ is —H, —C$_2$H$_5$ or —C$_2$H$_4$OH, and n is 0 or 1.

However, n is 0 when $R^1$ and $R^2$ are both —CH$_3$. n is also 0 (n=O), and $R^2$ is H, when $R^1$ is CH$_3$COO—. When $R^7$ is —C$_2$H$_5$ or —C$_2$H$_4$OH, n must be 0, and $R^1$ and $R^2$ must be —H.

Examples of diols of the foregoing formula include 1,2-ethanediol (ethylene glycol), 1,2-propanediol, 1,3-propanediol, 1,2-butanediol, 1,3-butanediol, 1,4-butanediol, 2,3-butanediol, 2-ethoxyethanol (ethylene glycol monoethyl ether), 2,2-oxy-bis-ethanol (diethylene glycol) and glycerol monoacetate.

Binary mixtures of any of the foregoing diol compounds and envelope disordering compounds, in a weight ratio of diol compound:cell envelope disordering compound of from about 1:1 to about 500:1, provide significant enhancement of penetration for a variety of nonpolar or lipophilic compounds, as well as a few compounds which appear to penetrate by both polar and nonpolar routes, and this ratio is therefore a preferred ratio. A ratio (envelope-disordering compound:diol) of from about 1:100 to about 1:10 for the combination is more preferred, and most preferably about 1:50 to about 1:10. The ratio most highly preferred is about 1:30 for the practice of this invention.

Nonsteroidal Anti-Inflammatory Agents

Nonpolar or lipophilic compounds which are especially useful when delivered by the vehicles of this invention are the nonsteroidal anti-inflammatory agents, including salicylic acid, ibuprofen, sulindac, naproxen, ketoprofen, etofenamate, and indomethacin, and their pharmaceutically acceptable salts and esters.

The nonsteroidal anti-inflammatory compounds of this invention comprise (a) from about 0.01% to about 35% by weight of a nonsteroidal anti-inflammatory drug;

(b) from 0% to about 70% by weight ethanol or 2-propanol; and (c) from about 5% to about 99%, especially from about 5% to about 75%, by weight of a penetration-enhancing carrier consisting essentially of
(i) a diol compound of the formula

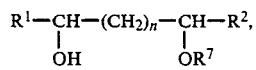

wherein $R^1$ is —H, —CH$_3$ or CH$_3$COO—, $R^2$ is —H or —CH$_3$, $R^7$ is —H, —C$_2$H$_5$ or —C$_2$H$_4$OH, and n is 0 or 1; provided that n is 0 when $R^1$ and $R^2$ are both CH$_3$; provided further that n is 0 when $R^1$ is CH$_3$COO—, and $R^2$ is —H; and provided further that n is 0, and $R^1$ and $R^2$ are both —H, when $R^7$ is either —C$_2$H$_5$ or —C$_2$H$_4$OH; and
  (ii) a cell envelope-disordering compound of the formula $R^3$—X,
wherein $R^3$ is a straight-chain alkyl of about 7 to about 16 carbon atoms, a non-terminal alkenyl of about 7 to about 22 carbon atoms, or a branched-chain alkyl of from about 13 to about 22 carbon atoms, and X is —OH, —COOCH$_3$, —COOC$_2$H$_5$, —OCOCH$_3$, —SOCH$_3$, —P(CH$_3$)$_2$O, —COOC$_2$H$_4$OC$_2$H$_4$OH, —COOCH(CHOH)$_4$CH$_2$OH, —COOCH$_2$CHOHCH$_3$, —COOCH$_2$CHOHCH$_2$OH, —(OCH$_2$CH$_2$)$_m$OH, or —COOR$^4$, or

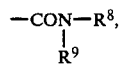

where $R^4$ is —H, —CH$_3$, —C$_2$H$_5$, —C$_3$H$_7$ or —C$_2$H$_4$OH, $R^8$ is —H, —CH$_3$, —C$_2$H$_5$, —C$_3$H$_7$ or —C$_2$H$_4$OH, $R^9$ is —H, —CH$_3$, —C$_2$H$_5$, —C$_3$H$_7$ or —C$_2$H$_4$OH, and m is 2-6; provided that when $R^3$ is an alkenyl and X is —OH or —COOH, at least one double bond is in the cis-configuration; the ratio of cell envelope-disordering compound:diol compound being in the range of from about 1:1 to about 1:500 by weight.

Among the nonsteroidal anti-inflammatory agents, few have the safety and efficacy record accumulated by the salicylates. Thus, salicylic acid and its common derivatives, such as aspirin, glycol salicylate, salicylamide, etc., are particularly preferred embodiments of the nonsteroidal anti-inflammatory compositions herein. Another especially preferred nonsteroidal anti-inflammatory drug, particularly for patients with sensitivity to salicylates, is indomethacin, as well as its common salts and esters. A particularly preferred form of indomethacin is indomethacin methyl ester.

Local Anesthetics

Another group of lipophilic pharmacologic actives whose penetration is significantly enhanced from the compositions of the present invention are the local anesthetics, including, without limitation, lidocaine, procaine, mepivacaine, bupivacaine, dibucaine, and tetracaine, as well as their pharmaceutically acceptable salts and esters.

The local anesthetic compositions of this invention comprise
(a) from about 0.01% to about 35% by weight of a local anesthetic;
(b) from 0% to about 70% by weight ethanol or 2-propanol; and
(c) from about 5% to about 99% by weight of a penetration-enhancing carrier consisting essentially of
(i) a diol compound of the formula

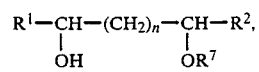

wherein $R^1$ is —H, —CH$_3$ or CH$_3$COO—, $R^2$ is —H or —CH$_3$, $R^7$ is —H, —C$_2$H$_5$ or —C$_2$H$_4$OH, and n is 0 or 1; provided that n is 0 when $R^1$ and $R^2$ are both CH$_3$; provided further that n is 0 and $R^2$ is —H, when $R^1$ is CH$_3$COO—; and provided further that n is 0 and $R^1$ and $R^2$ are both —H, when $R^7$ is either —C$_2$H$_5$ or —C$_2$H$_4$OH; and
  (ii). a cell envelope-disordering compound of the formula $R^3$—X
wherein $R^3$ is a straight-chain alkyl of about 7 to about 16 carbon atoms, a non-terminal alkenyl of about 7 to about 22 carbon atoms, or a branched-chain alkyl of from about 13 to about 22 carbon atoms, and X is —OH, —COOCH$_3$, —COOC$_2$H$_5$, —OCOCH$_3$, —SOCH$_3$, —P(CH$_3$)$_2$O, —COOC$_2$H$_4$OC$_2$H$_4$OH, —COOCH(CHOH)$_4$CH$_2$OH, —COOCH$_2$CHOHCH$_3$, —COOCH$_2$CHOHCH$_2$OH, COCH$_1$CH$_2$)$_m$OH, or —COOR$^4$ or

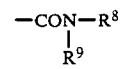

where $R^4$ is —H, —CH$_3$, —C$_2$H$_5$, —C$_3$H$_7$ or —CH$_2$H$_4$OH, $R^8$ is —H, —CH$_3$, —C$_2$H$_5$, —C$_3$H$_7$ or —C$_2$H$_4$OH, $R^9$ is —H, —CH$_3$, —C$_2$H$_5$, —C$_3$H$_7$ or —C$_2$H$_4$OH, and m is 2-6; provided that when $R^3$ is an alkenyl and X is —OH or —COOH, at least one double bond is in the cis-configuration; the ratio of diol compound:cell envelope-disordering compound being in the range of from about 1:1 to about 500:1 by weight. Among the local anesthetics, few have the safety and efficacy record accumulated by lidocaine. Thus, lidocaine is an especially preferred pharmacological active for use in the local anesthetic compositions of this invention. However, depending upon particular sensitivities of individual patients, and the desired duration of local anesthetic effects, other local anesthetics may be preferable in individual instances.

Antibiotics

Another group of compounds having pharmacologic activity which is especially suitable for topical administration by the compositions provided herein are the antibiotics, including, without limitation, erythromycin, penicillin, clindamycin, tetracycline, and chloramphenicol, as well as their pharmaceutically acceptable salts and esters. Of these, erythromycin, clindamycin, and tetracycline are especially useful, and preferred, for the antibiotic treatment of acne. Another commonly employed topical antibacterial mixture is a combination of polymyxin B, bacitracin, and enomycin. This composition is also suitable for administration with enhanced penetration via the compositions of this invention.

The antibiotic compounds of this invention comprise
(a) from about 0.01% to about 35% by weight of an antibiotic agent;
(b) from 0% to about 70% by weight ethanol or 2-propanol; and
(c) from about 5% to about 99% by weight of a penetration-enhancing carrier consisting essentially of
(i) a diol compound of the formula

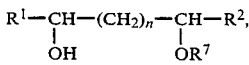

wherein $R^1$ is —H, —$CH_3$ or $CH_3COO$—, $R^2$ is —H, or —$CH_3$, $R^7$ is —H, —$C_2H_5$ or —$C_2H_4OH$ and n is 0 or 1; provided that n is 0 when $R^1$ and $R^2$ are both —$CH_3$; provided further than n is 0, and $R^2$ is —H, when $R^1$ is $CH_3COO$—, and provided further than n is 0, and $R^1$ and $R^2$ are both —H, when $R^7$ is either —$C_2H_5$ or —$C_2H_4OH$; and (ii) a cell envelope-disordering compound of the formula $R^3$—X wherein $R^3$ is a straight-chain alkyl of about 7 to about 16 carbon atoms, a non-terminal alkenyl of about 7 to about 22 carbon atoms, or a branched-chain alkyl of from about 13 to about 22 carbon atoms, and X is —OH, —$COOCH_3$, —$COOC_2H_5$, —$OCOCH_3$, —$SOCH_3$, —$P(CH_3)_2O$, —$COOCH_2CHOHCH_2OH$, —$(OCH_2CH_2)_mOH$, —$COOR^4$, or

where $R^4$ is —H, —$CH_3$, —$C_2H_5$, —$C_3H_7$ or —$C_2H_5OH$, $R^8$ is —H, —$CH_3$, —$C_2H_5$, —$C_3H_7$ or —$C_2H_5OH$, $R^9$ is —H, —$CH_3$, —$C_2H_5$, —$C_3H_7$ or —$C_2H_5OH$, and m is 2–6; provided than when $R^3$ is an alkenyl and X is —OH or —COOH, at least one double bond is in the cis-configuration; the ratio of diol compound: cell envelope-disordering —$COOC_2H_4OC_2H_4OH$, —$COOCH(CHOH)_4CH_2OH$, —$COOCH_2CHOHCH_3$, compound being in the range of from about 1:1 to about 500:1 by weight.

In dealing with non-acneiform dermatologic infections, penicillin is the almost universal drug of first choice. Accordingly, penicillin, which, when used herein, includes the synthetic penicillins, particularly the penicillinase-resistant varieties, also forms an especially preferred embodiment of the antibiotic compositions of this invention. Another agent which is especially preferred for systemic use, particularly in patients with sensitivity to the penicillins, is erythromycin, including its common pharmaceutical salts and esters. Examples would include erythromycin ethyl succinate, erythromycin lactobionate, erythromycin estolate, and the like. A third, particularly preferred composition, widely used in topical antibiotic ointments, is the combination of polymyxin B, bactitracin, and neomycin.

Benzoyl Peroxide

Another material especially suitable for administration with the penetration enhancers of this invention is benzoyl peroxide. However, because benzoyl peroxide is a powerful oxidizing agent, it cannot be used with the unsaturated envelope-disordering compounds since it readily oxidizes the unsaturated sites. Thus, when used with benzoyl peroxide, the membrane disordering compound has the formula $R^5$—X, where $R^5$ is a straight chain alkyl of from about 7 to about 14 carbon atoms, or a branched-chain alkyl with about 13 to about 22 carbon atoms, where X is —OH, —$COOCH_3$, —$COOC_2H_5$, —$OCOCH_3$, —$SOCH_3$, —$P(CH_3)_2O$, —$COOCH_2CHOHCH_3$, —$COOCH_2CHOHCH_2OH$, —$COOC_2H_4OC_2H_4OH$, —$(OCH_2CH_2)_mOH$, —$COOCH(CHOH)_4CH_2OH$, or —$COOR^4$ or

where $R^4$ is —H, —$CH_3$, —$C_2H_5$, —$C_3H_7$ or —$C_2H_4OH$, $R^8$ is —H, —$CH_3$, —$C_2H_5$, —$C_3H_7$ or —$C_2H_4OH$, $R^9$ is —H, —$CH_3$, —$C_2H_3$, —$C_3H_7$, or —$C_2H_4OH$, and m is 2–6.

Benzoyl peroxide is an item of commerce. It is preferably incorporated at levels from about 0.5% to about 25%, more preferably from about 1% to about 15%, and most preferably from about 2% to about 10%. In general, when formulating compositions for topical administration of benzoyl peroxide, the more benzoyl peroxide the better, the limiting factor usually being the skin irritation which commonly accompanies benzoyl peroxide administration.

The benzoyl peroxide compositions of this invention comprise (a) from about 0.01% to about 35% by weight benzoyl peroxide;
(b) from 0% to about 70% by weight ethanol or 2-propanol; and
(c) from about 5% to about 99% by weight of a penetration enhancing carrier consisting essentially of
(i) a diol compound of the formula

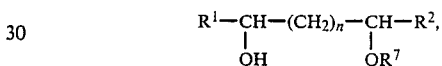

wherein $R^1$ is —H, —$CH_3$ or $CH_3COO$—, $R^2$ is —H or —$CH_3$, $R^7$ is —H, —$C_2H_5$, or —$C_2H_4OH$, and n is 0 or 1; provided that n is 0 when $R^1$ and $R^2$ are both —$CH_3$; provided further than n is 0 and $R^2$ is —H, when $R^1$ is $CH_3COO$—H; and provided further that n is 0, and $R^1$ and $R^2$ are both —H, when $R^7$ is either —$C_2H_5$ or —$C_2H_4OH$; and (ii) a cell envelope-disordering compound of the formula $R^5$—X, wherein $R^5$ is a straight-chain alkyl of from about 7 to about 16 carbon atoms, or a branched-chain alkyl of from about 13 to about 22 carbon atoms, and X is —OH, —$COOCH_3$, —$COOC_2H_5$, —$OCOCH_3$, —$SOCH_3$, —$P(CH_3)_2O$, —$COOC_2H_4OC_2H_4OH$, —$COOCH(CHOH)_4CH_2OH$, —$COOCH_2CHOHCH_3$, —$COOCH_2CHOHCH_2OH$, $(OCH_2CH_2)_mOH$, or —$COOR^4$, or

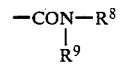

where $R^4$ is —H, —$CH_3$, —$C_2H_5$, —$C_3H_7$ or —$C_2H_4OH$, $R^8$ is —H, —$CH_3$, —$C_2H_5$, —$C_3H_7$ or —$C_2H_4OH$, $R^9$ is —H, —$CH_3$, —$C_2H_5$, —$C_3H_7$ or —$C_2H_4OH$, and m is 2–6; the ratio of cell envelope-disordering compound:diol compound being in the range of from about 1:1 to about 1:500 by weight.

The compositions are typically prepared by thoroughly blending all of the components together in admixture, and milling, if necessary, to reduce all particles of benzoyl peroxide to impalpable size (typically less than 0.25 mm). The benzoyl peroxide should be of high purity, on the order of 97% to 100% pure, and in the form of a finely divided powder. The powder may be either wet or dry, but is preferably wet for ease of handling and safety. If wet benzoyl peroxide is used, it may be necessary to grind the crystals before admixture or to mill the composition after admixture and blending to reduce the crystals to impalpable size. Preferably, the milling or grinding operation is performed with cooling to prevent decomposition of the peroxide by localized friction.

METHODS OF USE

It can be seen that this invention provides a method for treating and preventing pain and inflammation in humans and lower animals, comprising applying topically to a human or lower animal in need of such treatment a safe and effective amount of a composition according to this invention, containing a safe and effective amount of at least one of the nonsteroidal anti-inflammatory agents.

This invention also provides a method for treating and preventing pain in human and lower animals, comprising topically applying to a human or lower animal in need of such treatment a safe and effective amount of the composition of the present invention containing a safe and effective amount of at least one of the aforementioned local anesthetics.

This invention further provides a method for treating and preventing bacterial infection in humans and lower animals, comprising applying topically, to a human or lower animal in need of such treatment, a safe and effective amount of the composition of this invention containing at least one of the aforementioned antibiotic agents.

Finally, this invention also provides a method for treating or preventing acne, comprising applying to the afflicted situs a safe and effective amount of a benzoyl peroxide composition as provided herein. As mentioned, the present invention also provides compositions and methods ideally suited for the antibiotic treatment of acne.

The compositions of this invention are typically applied twice daily to the afflicted situs, or, when systemic effects are desired, to larger areas, depending upon the dose desired. A typical safe and effective usage rate is about 1 mg of the total composition/cm$^2$ skin to about 10 mg/cm$^2$ skin, per application, but this can vary with the use, the severity of the affliction, and the nature and concentration of pharmacological active, as well as the particular composition of the topical carrier being used. In particular, substantially higher application rates (up to 500 mg/cm$^2$) can be employed in conjunction with occlusive dressings.

The compositions can be applied qd, q12h, q8h, q6h, q4h, or on any other convenient treatment regimen. A q4h schedule is particularly preferred because it minimizes the amount of drug which is applied at one time, without requiring inordinately frequent applications or amounts of the composition which are too small to be applied conveniently.

By "topical administration" herein is meant directly laying on or spreading on epidermal tissue, especially outer skin.

By "safe and effective amount" of the compositions herein is meant a sufficient amount of the composition to alleviate or prevent the disease state being treated at a reasonable benefit/risk ratio attendant with any medical treatment. Within the scope of sound medical judgment, the amount of pharmaceutical active used will vary with the particular condition being treated, the severity of the condition, the duration of the treatment, the specific compound employed and its concentration, and like factors within the specific knowledge and expertise of the patient or the attending physician.

By "toxicologically or pharmaceutically acceptable" herein is meant ingredients which are suitable for use in contact with the tissues of humans and lower animals without undue toxicity, irritation, allergic response, and the like, commensurate with a reasonable benefit/risk ratio.

By the term "comprising" herein is meant that various other compatible drugs and medicaments, as well as inert ingredients and cosmetic vehicles, can be conjointly employed in the compositions and processes of this invention, as long as the critical binary penetration enhancement vehicle and pharmaceutical active are used in the manner disclosed herein. The term "comprising" thus encompasses and includes the more restrictive terms "consisting of" and "consisting essentially of" which characterize the use of the essential ingredients in the manner disclosed herein.

By "afflicted situs" herein is meant a localized area of inflammation or lesion, and the immediate surrounding area. By "acne" herein is meant common acne, acne vulgaris, in all forms, including papular, pustular or cystic.

By "nonsteroidal anti-inflammatory drug" is meant, generally, those drugs which appear to act, at least in part, by inhibition of prostaglandin synthetase. The variety of compounds encompassed by this phrase is well known to those of skill in the art, and reference may be had to standard texts, including *Antiinflammatory Agents, Chemistry and Pharmacology* Vol. 1, R. A. Scherrer, et al., Eds., Academic Press, New York, 1974, the disclosures of which are hereby incorporated herein by reference, for detailed disclosures of chemical structures, syntheses, side effects, etc.

By "penetration-enhancing" herein is meant that the binary penetration enhancing carriers of this composition provide marked transepidermal delivery of an incorporated pharmacological active, when compared to other compositions at equal chemical potential. This latter aspect is important, since varying solubilities of drugs in different vehicles will necessarily affect their transport across skin. Thus, for example, if a drug is soluble in vehicle A to the extent of 24%, and in vehicle B to the extent of 4%, if the compositions were to be compared at equal percentage concentration, rather than equal chemical potential, the lower solubility carrier will show a misleading six-fold difference in transport over the more soluble vehicle. The simplest way of assuring equal chemical potential for evaluating penetration enhancement is to use saturated solutions or solutions of equal percentage of saturation of pharmacological active in the various vehicles.

By "nonterminal alkenyl" herein is meant that the double bond is not found between the last two carbons in the hydrocarbon tail of the compound; terminal alkenyls are, from a structural standpoint, almost identical to fully saturated compounds, since the double bond, while rigid, does not affect the configuration of the chain.

By the "cis- configuration" herein is meant that both portions of the hydrocarbon chain are positioned on the same side of the double bond.

By "local anesthetic" herein is meant drugs that block nerve conduction when applied locally to nerve tissue in appropriate concentrations. They act on any part of the nervous system and on every type of nerve fiber.

Their action is reversible, their use being followed by complete recovery in nerve function with no evidence of structural damage to nerve fibers or cells.

By "antibiotic agent" herein is meant a chemical substance produced by microorganisms or a derivative of a chemical substance produced by microorganisms that has the capacity, in dilute solutions, to inhibit the growth of other microorganisms or destroy them.

INDUSTRIAL APPLICABILITY

Penetration-Enhancing Carriers

The topical penetration-enhancing carrier consists essentially of two critical ingredients, a $C_3$-$C_4$ diol compound of the formula $$R^1-\underset{OH}{CH}-(CH_2)_n-\underset{OR^7}{CH}-R^2,$$

wherein $R^1$ is —H, —$CH_3$, or $CH_3COO$—, $R^3$ is —H or —$CH_3$, $R^7$ is —H, —$C_2H_5$ or —$C_2H_4OH$, and n is 0 or 1; provided that n is 0 when $R^1$ and $R^2$ are both —$CH_3$; provided further that n is 0 and $R^2$ is —H, when $R^1$ is $CH_3COO$—; and provided further that n is 0, and $R^1$ and $R^2$ are both —H, when $R^7$ is either —$C_2H_5$ or —$C_2H_4OH$; and a cell envelope-disordering compound of the formula $R^3$—X wherein $R^3$ is a straight chain alkyl of from about 7 carbon atoms to about 22 carbon atoms, a non-terminal alkenyl of from about 7 to about 22 carbon atoms, or a branched-chain alkyl of from about 15 carbon atoms to about 22 carbon atoms, and X is —OH, —COOCH$_3$, —COOC$_2$H$_5$, —OCOCH$_3$, —OH, —SOCH$_3$, —P(CH$_3$)$_2$O, —COOC$_2$H$_4$OC$_2$H$_4$OH, —COOCH(CHOH)$_4$CH$_2$OH, —COOCH$_2$CHOHCH$_3$, —COOCH$_2$CHOHCH$_2$OH, (OCH$_2$CH$_2$)$_m$OH, or —COOR$^4$, or $$\underset{R^9}{\underset{|}{CON}}-R^8,$$

where $R^4$ is —H, —$CH_3$, —$C_2H_5$, —$C_3H_7$ or —$C_2H_5OH$, $R^8$ is —H, —$CH_3$, —$C_2H_5$, —$C_3H_7$ or —$C_2H_5OH$, $R^9$ is —H, —$CH_3$, —$C_2H_5$, —$C_3H_7$ or —$C_2H_5OH$, and m is 2-6; provided than when $R^3$ is an alkenyl and X is —OH or —COOH, at least one double bond must be in the cis-configuration.

Preferred ratios for combinations of envelope-disordering compound:diol in the present invention are from about 1:1 to about 1:500. More preferably a ratio of about 1:10 to about 1:100 of cell envelope-disordering compound to diol should be employed in the present invention. Most preferably about 1:10 to about 1:50 are used, with a ratio of 1:30 being most highly preferred in the instant invention.

The compositions herein typically contain from about 0.05% to about 50% of the envelope-disordering compounds as described above. Of these, myristyl alcohol, methyl myristate, methyl laurate, ethyl myristate, ethyl laurate, myristyl acetate, and laurylacetate are preferred. The most preferred envelope-disordering compounds are methyl myristate, methyl laurate, ethyl myristate, ethyl laurate, myristyl acetate, and lauryl acetate, with methyl myristate and methyl laurate being especially preferred. These esters are preferably present in the composition at a concentration of about 0.05% to about 5% by weight, most preferably about 1% to about 3% by weight.

In addition to those parameters well-known to one skilled in the art of the present invention, such as cost, availability, solvent properties, solute properties, stability, and the like, the preferred cell envelope-disordering compounds of the instant invention possess the ability to enhance integument penetration while exhibiting little dermal irritation. While some dermal irritation is acceptable in the practice of this invention, the most preferred cell envelope-disordering compounds show less irritation alone than the sum of the irritation caused by the remaining total composition absent the cell envelope-disordering compound. Of course, a cell envelope-disordering compound that causes no noticeable dermal irritation is most highly preferred.

The compositions also typically contain from about 5% to about 98% by weight of a diol. 1,2-propanediol (propylene glycol) and 2,2'-oxy-bis-ethanol (diethylene glycol) are the preferred diols. The most preferred diol is 1,2-propanediol. The diol component is preferably present at a concentration of from about 10% to about 50% by weight, most preferably from about 20% to about 30% by weight.

The compositions typically contain a cosmetically acceptable solvent such as ethanol or isopropanol. The solvent, if one is used, should preferably evaporate rapidly and completely to leave only the active components of the composition at the site of application.

It can be seen from the foregoing that the compositions of the present invention admit of considerable variation, so long as the critical components of active drug, diol compound, and envelope-disordering compounds are present.

In some cases, solubility of the envelope-disordering compounds imposes a limitation on formulation. More specifically, solubility of these compounds in typical compositions decreases with increasing chain length. For example, n-decanol is generally soluble in the diol compounds of this invention up to about 50% by weight. Lauryl alcohol will be found to be soluble in the same compositions only up to about 20-25% by weight. In general, the envelope-disordering compounds are soluble at concentrations which are more than adequate to enhance penetration of the active drug, and, in general, high concentrations tend to cause skin irritation without a commensurate increase in penetration enhancement. Indeed, at very high levels, penetration enhancement begins to fall off, as the levels of auxiliary compound reduce the concentration of the equally necessary diol compound.

In cases where solubility of one or more components creates a problem in formulation, all of the components will generally be soluble in ethanol, and the use of ethanol as a co-solvent in formulation is especially recommended.

Other optional components can be added to the formulations of this invention in minor amounts to enhance their cosmetic acceptability. Such components include thickening agents, such as methyl cellulose, cross-linked carboxypolymethylene polymers, bentonite, gum tragacanth, gum karaya, and polyethylene glycols. Such thickening agents are generally employed at a level of from about 1% to about 10% of the composition. Cosmetic resins and film formers such as the Carboset carboxyvinyl polymers can also be present. Small amounts of pigments and opacifiers, such as zinc oxide, and fragrance materials such as perfumes can also be used.

Such formula modifications are well within the skill of workers in the cosmetic and dermatological arts, and, by themselves, constitute no part of the present invention. Many additives which enhance cosmetic acceptability undesirably interfere with penetration enhancement. Therefore, the use of the foregoing, and other, optional ingredients is preferably avoided.

The following examples illustrate the broad range of utility of the compositions of the present invention, while not intending to limitative thereof.

Skin Penetration Studies

In Examples I–III, enhancement of penetration through the skin of rats was determined by applying the indicated formulations, containing radiolabeled drug active to a protected site on the back of rats and measuring the amount of radioactivity in the urine. In Examples IV—XIII, human skin (heat-separated abdominal epidermis, taken at autopsy) was placed in a standard Franz diffusion apparatus (Crown Glass Co., Somerville, N.J.) in a horizontal position between a lower, capped diffusion cell and an upper, open cell. A normal saline solution was added to the lower diffusion cell, abutting the subcutaneous side of the skin, and the test composition comprising a solution of active drug in the carrier at indicated formulation was added to the diffusion cell abutting the epidermal side of the skin.

This cell assembly was kept in a constant-temperature room at about 31° C. At appropriate intervals, each diffusion cell assembly was opened and the diffusate from the cell abutting the subcutaneous side of the skin was withdrawn. Drug active in the diffusate was measured using standard analytical techniques.

EXAMPLES I–II

These studies compared the effects of a diol, propylene glycol (PG), alone, an envelope-disordering compound, myristyl alcohol (MA), alone, and the combination of PG+MA, on skin penetration of 1% benzoyl peroxide and 2% indomethacin.

I

| Vehicle | 2% Indomethacin Penetration | Enhancement Factor |
|---|---|---|
|  | ug/cm²hr. |  |
| MA 3% + solvent to 100% | 0.23 ± .14 | 0.43 |
| PG 30% + solvent to 100% | 0.54 ± .32 | 1.00 |
| MA 3% + PG 30% + solvent to 100% | 1.92 ± .79 | 3.56 |

II

| Vehicle | 1% Benzoyl Peroxide % Recovery |
|---|---|
| None (Solvent alone) | 0.33 ± .16 |
| MA 1.5% + solvent to 100% | 1.51 ± .48 |
| PG 20% + solvent to 100% | 3.76 ± 1.63 |
| MA 1.5% + PG 20% + solvent to 100% | 14.09 ± 4.66 |

EXAMPLES III–VI

The following studies compared the efficacy of various diol compounds with a single envelope disordering compound and a single pharmacologic active.

III

| | 2% Indomethacin, 1% MA |
|---|---|
| Diol compound - 97% | 72 Hr. Penetration, $\mu g/cm^2$ hr. |
| 1,2-propanediol | 0.81 ± .28 |
| 1,3-propanediol | 0.73 ± .25 |
| 1,2-butanediol | 0.63 ± .05 |
| 1,3-butanediol | 0.84 ± .12 |
| 1,4-butanediol | 1.22 ± .21 |

IV

| | Saturated Salicyclic Acid (SA) .25 Mole Fraction Oleic Acid/Diol |
|---|---|
| Vehicle | Relative Transport |
| 23% SA + PG to 100% | 1 |
| 15% SA + PG/oleic acid to 100% | 15 |
| 23% SA + 1,2-butanediol to 100% | 1 |
| 15% SA + 1,2-butanediol/oleic acid to 100% | 5 |
| 21% SA + 1,3-butanediol to 100% | 0.5 |
| 15% SA + 1,3-butanediol/oleic acid to 100% | 5 |
| 28% SA + 2,3-butanediol to 100% | 0.5 |
| 17% SA + 2,3-butanediol/oleic acid to 100% | 5 |
| 14% SA + 1,2-hexanediol to 100% | 1 |
| 24% SA + 1,2-hexanediol/oleic acid to 100% | 1 |
| 19% SA + 1,2-octanediol to 100% | 1 |
| 27% SA + 1,2-octanediol/oleic acid to 100% | 1 |

V

| | 1% Indomethacin (Indo) 2-3% Myristyl Alcohol (MA) |
|---|---|
| Vehicle | Relative Penetration |
| 1% Indo + 30/70 PG/EtOH to 100% | 1 |
| 1% Indo + 2% MA + 30/70 PG/EtOH to 100% | 7 |
| 1% Indo + 30/70 PEG 400/EtOH to 100% | .06 |
| 1% Indo + 1% MA + 30/70 PEG 400/EtOH to 100% | 0.3 |
| 1% Indo + 15/15/70 PG/PEG 400/EtOH to 100% | 0.3 |
| 1% Indo + 2% MA + 15/15/70 PG/PEG 400/EtOH to 100% | 0.6 |
| 1% Indo + 30/70 2-methyl-2,4 pentanediol/EtOH to 100% | 0.3 |
| 1% Indo + 2% MA + 30/70 2-methyl-2,4-pentanediol/EtOH to 100% | 0.3 |
| 1% Indo + 30/70 1,3-Propanediol/EtOH to 100% | 0.3 |
| 1% Indo + 3% MA + 30/70 1,3-propanediol/EtOH to 100% | 7 |
| 1% Indo + 30/70 Glycerol/EtOH to 100% | 0.1 |
| 1% Indo + 3% MA + 30/70 Glycerol/EtOH 100% | 0.4 |

EXAMPLE VI

| Vehicle | Dose | Relative Penetration |
|---|---|---|
| 1% Indo + 30/70 PG/EtOH to 100% | 250 µl/cm² | 1 ± 55% |
| 1% Indo + 30/70 DEG/EtOH1.8 6 to 100% |  | .4 ± 30% |
| 1% Indo + 1% MA + 30/70 PG/EtOH to 100% |  | 1.8 ± 65% |
| 1% Indo + 1% MA + 30/70 DEG/EtOH to 100 |  | 4.0 ± 15% |
| 1% Indo + 1% MA + 30/70 PG/EtOH to 100% | 25 µl/cm² | .1 ± 75% |
| 1% Indo + 1% MA + 30/70 DEG/EtOH to 100% |  | .4 ± 25% |

EXAMPLE VII

The following data show the effectiveness of various fatty acid esters and fatty alcohol acetate as penetration aids for indomethacin.

| Vehicle | Dose | Relative Penetration |
|---|---|---|
| 1% Indo + 30/70 PG/EtOH to 100% | 25 µl/cm$^2$ | 1 ± 30% |
| 1% Indo + 30/70 PG/EtOH + 1% MA | | 5 ± 20% |
| 1% Indo + 3% lauryl acetate + 30/70 PG/EtOH to 100% | | 5 ± 30% |
| 1% Indo + 3% ethyl laurate + 30/70 PG/EtOH to 100% | | 6 ± 50% |
| 1% Indo + 3% ethyl myristate + 30/70 PG/EtOH to 100% | | 4 ± 40% |
| 1% Indo + 3% myristyl acetate + 30/70 PG/EtOH | | 5 ± 30% |

EXAMPLE VIII

The following data illustrate the effects of a variety of envelope-disordering compounds with a single diol compound and a single pharmacologic active.

| Salicylic Acid added to Saturation | |
|---|---|
| Vehicle | Relative Penetration |
| Propylene glycol (saturated with salicylic acid) | 1 |
| .25 mole fraction oleic acid/PG (saturated with SA) | 17 |
| .25 mole fraction isostearyl alcohol/PG (saturated) | 12 |
| .25 mole fraction octanol/PG (saturated) | 9 |
| .25 mole fraction PG monoisostearate/PG (saturated) | 13 |
| .25 mole fraction isostearyldiethoxy ether (saturated) | 12 |
| Methyl oleate saturated with PG (in turn saturated with salicylic) | 5 |
| Farnesol (saturated) | 1 |
| 50/50 PG/Farnesol (saturated) | 10 |
| Geraniol (saturated) | 2 |
| 50/50 PG/Geraniol (saturated) | 10 |
| Phytol (saturated) | 1 |
| 50/50 PG/Phytol (saturated) | 10 |
| Monoacetin (saturated) | 1 |
| Monoacetin + 3% C$_{14}$OH (saturated) | 2 |
| PG + 3% C$_{14}$OH (saturated) | 3 |

EXAMPLE IX

The following data illustrate the effect of chain length and multiple unsaturation of the envelope-disordering compound on the skin penetration of 1% salicylic acid in propylene glycol (PG)

| Vehicle | Relative Flux |
|---|---|
| 99% Propylene glycol + 1% salicylic acid (PG) | 1 |
| 98% PG + 1% 0.1 M 9-cis-tetradecenoic acid + 1% SA | 9 |
| 98% PG + 1% 0.1 M 9-cis-hexadecenoic acid + 1% SA | 8 |
| 98% PG + 1% 0.1 M 10-cis-heptadecenoic acid + 1% SA | 7 |
| 98% PG + 1% 0.1 M 10-cis-octadecenoic acid + 1% SA | 7 |
| 98% PG + 1% 0.1 M 9-cis-octadecenoic acid + 1% SA | 7 |
| 98% PG + 1% 0.1 M 11-cis-octadecenoic acid + 1% SA | 9 |
| 98% PG + 1% 0.1 M 9-cis-12-cis-octadecadienoic acid + 1% SA | 8 |
| 98% PG + 1% 0.1 M 9-trans-12-trans-octadecadienoic acid + 1% SA | 6 |
| 98% PG + 1% 0.1 M 9-cis-12-cis-15-cis-octadecatrienoic acid + 1% SA | 8 |
| 98% PG + 1% 0.1 M 11-cis-eicosenoic acid + 1% SA | 6 |

EXAMPLE X

The following data illustrate the importance of cis-double bonds, compared to trans-, in penetration of 1% salicylic acid in 90/10 propylene glycol/1-propanol.

| Vehicle | Relative Flux |
|---|---|
| 99% 90/10 propylene glycol/1-propanol (90/10) + 1% salicylic acid | 1 |
| 98% 90/10 + 1% 0.1 M 9-cis-octadecenoic acid + 1% salicylic acid | 10 |
| 98% 90/10 + 1% 0.03 M 9-trans-octadecenoic acid + 1% salicylic acid | 2 |
| 98% 90/10 + 1% 0.1 M tetradecanoic acid + 1% salicylic acid | 1 |

EXAMPLE XI

The following data illustrate the effect of envelope-disordering compound chain length on enhancement of salicylic acid penetration.

| Vehicle | Relative Penetration |
|---|---|
| 1% SA in PG | 1 |
| 1% SA in PG + 1% .2M C$_{16}$OH | 1 |
| 1% SA in PG + 1% .2M C$_{14}$OH | 4 |
| 1% SA in PG + 1% .2M C$_{12}$OH | 9 |
| 1% SA in PG + 1% .2M C$_{10}$OH | 8 |
| 1% SA in PG + 1% .2M C$_8$OH | 2 |

EXAMPLE XII

The following data illustrate the effect of alkenyl methyl sulfoxides on skin penetration of salicylic acid in propylene glycol.

| Vehicle | Relative Flux |
|---|---|
| 99% Propylene glycol (PG) + 1% salicylic acid | 1 |
| 98% PG + 1% 0.1 M 9-cis-hexadecenyl MSO + 1% SA | 5 |
| 98% PG + 1% 0.1 M 6-cis-octadecenyl MSO + 1% SA | 10 |
| 98% PG + 1% 0.1 M 9-cis-octadecenyl MSO + 1% SA | 7 |
| 98% PG + 1% 0.1 M 9-trans-octadecenyl MSO + 1% SA | 7 |
| 98% PG + 1% 0.1 M 11-cis-octadecenyl MSO + 1% SA | 7 |
| 98% PG + 1% 0.1 M 13-cis-doconsenyl MSO + 1% SA | 6 |

EXAMPLES XIII-XIV

The following data illustrate the effect of varying concentrations of envelope-disordering compound on penetration of a single drug active from a single diol (propylene glycol).

XIII

| 0.5% Indomethacin Varied % Concentrations Myristyl Alcohol | |
|---|---|
| Vehicle | Relative Penetration |
| .5% Indomethacin in 99.5% PG | 1 |
| .5% Indomethacin + 0.3% MA + PG to 100% | 3 |
| .5% Indomethacin + 1% MA + PG to 100% | 8 |
| .5% Indomethacin + 3% MA + PG to 100% | 11 |

XIV

| Saturated Salicylic Acid Varying Mole Fractions of Oleic Acid | |
|---|---|
| Vehicle | Relative Flux |
| 19% Salicylic acid + PG to 100% | 1 |
| 3% Salicylic acid + oleic acid to 100% | 1 |
| 12% Salicylic acid + .25 MF oleic acid/PG to 100% | 10 |
| 6% Salicylic acid + .5 MF oleic acid/PG to 100% | 20 |
| 5% Salicylic acid + .75 MF oleic acid/PG to 100% | 12 |

The data of Example XIII also illustrate that the combination of diol and unsaturated acid produces marked enhancement of penetration over either component used alone.

EXAMPLE XV

The following data show the effectiveness of various fatty acid esters and fatty alcohol acetate as penetration aids for indomethacin.

| Vehicle | Dose | Relative Penetration |
|---|---|---|
| 1% Indo in 30/70 PG/EtOH | 25 1/cm² | 1 ± 30% |
| 1% Indo + 1% MA + 30/70 PG/EtOH to 100% | | 5 ± 20% |
| 1% Indo + 3% lauryl acetate + 30/70 PG/EtOH to 100% | | 5 ± 30% |
| 1% Indo + 3% ethyl laurate + 30/70 PG/EtOH to 100% | | 6 ± 50% |
| 1% Indo + 3% ethyl myristate + 30/70 PG/EtOH to 100% | | 4 ± 40% |
| 1% Indo + 3% myristyl acetate + 30/70 PG/EtOH to 100% | | 5 ± 30% |

FORMULATION EXAMPLE XVI

A gel is prepared having following formula

| | Wt. % |
|---|---|
| Lidocaine (diethylaminoacet-2,6-xylidide) | 2 |
| Propylene glycol | 30 |
| Stearyl alcohol | 5 |
| Hexadecenyl dimethyl phosphine oxide | 3 |
| Petrolatum | 1 |
| Polysorbate 80 | .5 |
| Carbomer 934 | .3 |
| Sodium Hydroxide 1N | 1.5 |
| H₂O | Bal. |

The components other than sodium hydroxide are simply mixed thoroughly. The sodium hydroxide, added last, causes the Carbomer to gel, and the composition is ready for use.

In use, this composition provides marked enhancement of lidocaine penetration through skin, to provide local anesthetic action in the treatment of pain or pruritus.

In the foregoing composition, the following drug actives can be substituted for the lidocaine, also with marked enhancement of skin penetration: procaine, dibucaine, bupivacaine, tetracaine, chloroprocaine, hexylcaine, mepivacaine, piperocaine, prilocaine, cyclomethylcaine, dimethisoquin, benzocaine, dyclonine, and pramoxine.

EXAMPLE XVII

A topical erythromycin preparation is formulated as follows:

| | Wt. % |
|---|---|
| Erythromycin base | 2 |
| Propylene glycol | 30 |
| Diethylene glycol oleate | 5 |
| Hydroxypropyl cellulose | 2 |
| H₂O | 20 |
| Ethanol | Bal. |

The components are simply mixed thoroughly and the composition is ready for use. This formulation is preferably refrigerated, to maintain stability of the erythromycin active. This composition provides enhanced skin penetration of the erythromycin active, for the treatment of acne, and for the treatment of systemic infections in those individuals who experience gastric upset as a side effect of oral erythromycin administration.

In the foregoing composition, the following drug actives can be substituted for the erythromycin base, also with enhanced skin penetration: Penicillin V, oxacillin, cephalothin, cefazolin, cephaloridine, cephalexein, tetracycline, chlortetracycline, oxytetracycline, doxycycline, chloramphenicol, neomycin, polymyxin B, and bacitracin. In each instance, the fundamental pharmacologic and toxicologic profile of the drug active remains unchanged, other than those aspects related to route of administration, such as nausea in oral administration, pain or burning on injection, etc..

EXAMPLE XVII

A benzoyl peroxide gel is formulated as follows

| Compound | % by Weight |
|---|---|
| Benzoyl Peroxide | 10 |
| Mristyl Alcohol | 2 |
| 1,2-Propanediol | 10 |
| Carbomer 940 | 1.35 |
| Carboset 514H* | 0.63 |
| NaOH | 0.35 |
| Ethanol | 13.5 |

-continued

| Compound | % by Weight |
|---|---|
| Water | Balance |

*Carbosets are anionic acrylic resins. Carbosets are sold by B. F. Goodrich and are described in McCutcheon's Detergents and Emulsifiers, North American Edition, 1978 Annual, page 78.

4.0 grams of Carbomer 940 are dispersed in 200 ml $H_2O$. To this solution is added 50 ml of ethanol. To this mixture is added about 6 pellets (ca. 0.6 g.) of sodium hydroxide. The mixture immediately gels. To a standard, commercially available solution of B. F. Goodrich Carboset 514H (30% active polymer in ammonia water) is added sufficient water to produce a solution containing 5% by weight of the active polymer. 50 ml of this dilute solution is added to the previously prepared gel and the mixture is stirred until a uniform gel is obtained.

To the gel so produced, the other components of the composition are mixed to achieve the desired concentration.

Complete mixing of the components is followed by cold milling using a colloid mill to reduce the particle size of the benzoyl peroxide. The final composition is effective yet reasonably mild to the skin.

The composition thus prepared is then applied as needed to the situs of affliction. Typically, the composition is applied morning and night with fingertips, pads, cotton balls, or the like.

EXAMPLE XIX

A topical indomethacin lotion is prepared by mixing the following ingredients:

| Compound | % by Weight |
|---|---|
| Indomethacin methyl ester | 2 |
| cis-linoleyl alcohol | 5 |
| Monoacetin | 40 |
| Ethanol | Balance |

This lotion applied to skin at a rate of from about 1 mg/cm² to about 5 mg/cm², every 4 hours, provides enhanced penetration of indomethacin across skin, to achieve clinically significant tissue levels of indomethacin.

In the foregoing lotion, the indomethacin ester active can be replaced by other nonsteroidal, anti-inflammatories, including, without limitation, salicyclic acid, methyl salicyclate, glycol salicyclate, benzyl-2,5-diacetoxy benzoic acid, ibuprofen, sulindac, naproxen, ketopropfen, estofenamate, phenylbutazone, and indomethacin and other compounds of the formula

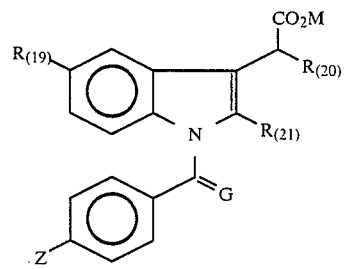

wherein $R^{19}$ is $CH_3O$, $(CH_3)_2H$, F or $CH_3$; $R^{20}$ and $R^{21}$ are H or $CH_3$, M is H, alkali metal or $C_1$-$C_{20}$ alkyl, alkenyl, or aryl, Z is halogen, $CF_3$, or $CH_3S$; and G is O or $H_2$.

What is claimed is:

1. A composition of matter for topical administration, said composition comprising
   (a) from about 0.5% to about 35% by weight of a nonsteroidal anti-inflammatory agent selected from the group consisting of salicylic acid, ibuprofen, sulindac, naproxen, ketoprofen, ethofenamate, and indomethacin, and the pharmaceutically-acceptable salts and esters thereof;
   (b) from 0% to about 70% by weight ethanol or 2-propanol; and
   (c) a penetration-enhancing carrier consisting essentially of
      (i) from about 10% to about 98% by weight of the composition of propylene glycol; and
      (ii) from about 1% to about 5% by weight of the composition of a cell envelope-disordering compound selected from the group consisting of methyl myristate, methyl laurate, methyl caprate, ethyl myristate, ethyl laurate, ethyl caprate, myristyl acetate, lauryl acetate and capric acetate.

2. The composition of claim 1 wherein the cell-envelope disordering compound is selected from the group consisting of methyl myristate, methyl laurate, ethyl myristate, ethyl laurate, myristyl acetate and lauryl acetate.

3. The composition of claim 1 wherein the nonsteroidal anti-inflammatory agent is ibuprofen.

4. The composition of claim 1 wherein the nonsteroidal anti-inflammatory agent is naproxen.

5. The composition of claim 1 wherein the nonsteroidal anti-inflammatory agent is ketoprofen.

6. The composition of claim 1 wherein the cell-envelope disordering compound is methyl laurate.

7. The composition of any of claim 1-6 wherein the concentration of the nonsteroidal anti-inflammatory agent is from about 1% to saturation in the composition.

8. A method for treating and preventing pain or inflammation in a human or lower animal, which method comprises applying topically to a human or lower animal in need of such treatment a safe and effective amount of a composition according to any of claims 1-6.

* * * * *

UNITED STATES PATENT AND TRADEMARK OFFICE
CERTIFICATE OF CORRECTION

PATENT NO. : 4,954,487
DATED : September 4, 1990
INVENTOR(S) : E.R. COPPER, M.E. LOOMANS and R.R. WICKETT It is certified that error appears in the above-identified patent and that said Letters Patent is hereby corrected as shown below:

Column 4, line 17, "monooesoarach" should be --monoisoarachidate--.

Column 6, line 23, "COCH$_1$CH$_2$)$_m$OH" should be -- -(OCH$_2$CH$_2$)$_m$OH --.

Column 7, line 20, after "-P(CH$_3$)$_2$O," should be inserted

-- -COOC$_2$H$_4$OC$_2$H$_4$OH, -COOCH$_2$(CHOH)$_4$CH$_2$OH, -COOCH$_2$CHOHCH$_3$,--.

Column 7, lines 33-34, after "cell envelope-disordering", delete

-- -COOC$_2$H$_4$OC$_2$H$_4$OH, -COOCH(CHOH)$_4$CH$_2$OH, -COOCH$_2$CHOHCH$_3$, --.

Column 11, line 44, "H$_5$OH," should be --H$_4$OH,--.

Column 11, line 45, "H$_5$OH," should be --H$_4$OH,--.

Column 11, line 46, "H$_5$OH," should be --H$_4$OH,--.

Signed and Sealed this

Twenty-third Day of June, 1992

Attest:

DOUGLAS B. COMER

Attesting Officer

Acting Commissioner of Patents and Trademarks